United States Patent [19]

Petroff et al.

[11] Patent Number: 5,145,977
[45] Date of Patent: Sep. 8, 1992

[54] POSTEMERGENT HERBICIDE COMPOSITIONS CONTAINING ACETOXY-TERMINATED SILICONE GLYCOL AND DISPERSANT

[75] Inventors: Lenin J. Petroff, Bay County; David J. Romenesko; Bradley C. Bahr, both of Midland, all of Mich.

[73] Assignee: Dow Corning Corporation, Midland, Mich.

[21] Appl. No.: 484,604

[22] Filed: Feb. 26, 1990

Related U.S. Application Data

[62] Division of Ser. No. 439,906, Nov. 21, 1989, Pat. No. 4,933,002.

[51] Int. Cl.$^5$ .................................. C07F 7/08
[52] U.S. Cl. ................................ 556/437; 71/116; 71/DIG. 1
[58] Field of Search ................. 71/116, DIG. 1; 556/437

[56] References Cited

U.S. PATENT DOCUMENTS

| | | | |
|---|---|---|---|
| Re. 31,455 | 12/1983 | Bayer et al. | 71/115 |
| 3,299,122 | 1/1967 | Bailey | 260/448.2 |
| 3,427,271 | 2/1969 | McKellar | 260/29.2 |
| 4,765,243 | 8/1988 | Schiefer et al. | 101/451 |

FOREIGN PATENT DOCUMENTS 1255249 10/1969 United Kingdom .

OTHER PUBLICATIONS

L. L. Jansen, Weed Science, v. 21, p. 130–135, Mar. 1973.
J. M. Balveaves, Proc. 39th New Zealand Weed and Pest Control Conference, pp. 98–101, 1985.
Union Carbide Corp., "Silicones for the Agricultural Industry" 1980.
Union Carbide Corp., "Surface Active Copolymers" 1983.
Union Carbide Corp., "Silwet(R) Surfactants for Use in Agriculture" 1980.

*Primary Examiner*—Richard L. Raymond
*Assistant Examiner*—B. Burn
*Attorney, Agent, or Firm*—Alexander Weitz

[57] ABSTRACT

There is disclosed a herbicide composition in which a postemergent herbicide is activated by the inclusion of a silicone glycol adjuvant consisting essentially of (i) a silicone glycol having an average structure

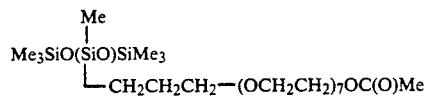

wherein Me denotes a methyl radical, and (ii) a silicone glycol dispersant compound for component (i). When compared to similar prior art silicone glycol adjuvants not having an acetoxy terminated glycol chain, the compositions of the present invention provide enhanced rainfastness in the control of weeds, particularly velvetleaf plants.

1 Claim, No Drawings

POSTEMERGENT HERBICIDE COMPOSITIONS CONTAINING ACETOXY-TERMINATED SILICONE GLYCOL AND DISPERSANT

This is a divisional of application Ser. No. 07/439,906, filed Nov. 21, 1989, now U.S. Pat. No. 4,933,002 issued Jun. 12, 1990.

This invention relates to postemergent herbicide formulations. More particularly, the present disclosure relates to a composition of a postemergent herbicide which is activated by the inclusion of a particular silicone glycol adjuvant consisting essentially of (i) a silicone glycol having an average of seven ethylene oxide units in its glycol chain, said glycol chain being terminated by an acetoxy group, and (ii) a silicone glycol dispersant compound.

BACKGROUND OF THE INVENTION

It is well recognized in the art that the full potency of a given organic herbicide is not generally attained without the inclusion of various adjuvants, an adjuvant being broadly defined as any substance which enhances the effectiveness of the herbicide. Thus, for example, through proper formulation with an activity-increasing adjuvant, the damage inflicted upon a particular plant species by an herbicide can be amplified many fold. Such an activity-increasing adjuvant does not generally have biological activity on its own but only brings out the activity of the herbicide.

An example of the aforementioned activity-increasing adjuvants is the class of surfactants known as silicone glycols. These liquids have been shown to enhance the efficacy of various herbicides. L. L. Jansen (Weed Science, v. 21, pages 130–135, March, 1973) examined the effect of adding various silicone glycol adjuvants to different herbicides and found that these adjuvants were superior to a standard organic surfactant in eight plant species. In this study, cationic amino silicone surfactants were also evaluated, but found to be less effective than the organic material. In any event, no specific structures of the silicone compounds were provided in this paper.

Great Britain Patent Number 1,255,249 to Dow Corning Corporation again discloses herbicide compositions employing silicone glycol copolymers. Here, general utility of a large number of adjuvants is professed, as exemplified by two generic silicone glycol formulas which embrace structures having both diorganosiloxane units and alkyl-glycol siloxane units. There is also provided a wide-ranging list of suitable herbicides. This reference, however, provides little direction to those skilled in the art as to which particular silicone glycol structures are to be advantageously combined with specific herbicides, save for two examples employing a triazine herbicide in conjunction with an adjuvant having 1.8 siloxy units and bearing a glycol chain having 12 ethylene oxide units.

In addition to the herbicidal enhancement provided by the activity-increasing adjuvants discussed above, it is often important that herbicide formulations retain a significant degree of activity when plants treated therewith are exposed to rain shortly after application, this being a definition of the degree of "rainfastness." This is particularly critical in the case of water-soluble postemergent herbicides, such as acifluorfen-sodium, which are easily washed away by rainfall occurring within about six hours of application. Typically, this problem is currently addressed by inclusion of another class or adjuvants in the herbicide formulation, namely "sticking agents." The main function of these materials, as the appellation implies, is to impart an increased measured of adhesion of the herbicide composition to plant foliage and thus prevent premature washing away should precipitation occur after the plants are sprayed. The sticking agents are usually polymeric compounds which are generally water-insoluble and tacky in nature.

Neither of the above references addresses the issue of rainfastness nor do these references suggest to those of ordinary skill in the art how particular silicone glycol compounds may be employed to provide both enhanced herbicidal activity to particular herbicides as well as increased rainfastness in the very same formulation, without resorting to the use of additional sticking agents.

In a copending application, Ser. No. 07/274,067, filed on Nov. 21, 1988, assigned to the assignee of the present invention and hereby incorporated by reference, it was shown that the rainfastness of a postemergent herbicide can be synergistically increased by the inclusion of a combination of a silicone glycol, and a dispersant for the silicone glycol, in the herbicide composition. Quite surprisingly, the improvement in rainfastness resulted only when the silicone glycol had an average of four or five ethylene oxide units in its glycol chain. Neither this silicone glycol nor the dispersants therefor, provided rainfastness when used as the sole adjuvant in conjunction with the herbicide.

SUMMARY OF THE INVENTION

It has now further been found that a particular silicone glycol, not specifically disclosed in the art, imparts an unexpectedly high degree of rainfastness to post emergent herbicides. The present invention therefore relates to a composition consisting essentially of:
(I) a postemergent herbicide; and
(II) from about 0.01 to 50 parts by weight, for each part by weight of said herbicide (I), of a silicone glycol adjuvant consisting essentially of
(i) from 20 to 95 weight percent of a silicone glycol having the average structure

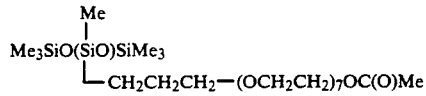

wherein Me denotes a methyl radical, and
(ii) from 80 to 5 weight percent of a silicone glycol dispersant having the average formula

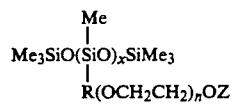

wherein Me has its above defined meaning, R is a divalent alkylene group having 2 to 6 carbon atoms, Z is selected from the group consisting of hydrogen, an alkyl radical having 1 to 3 carbon atoms and an acyl group having 2 to 4 carbon atoms, n is 8 to 24 and x is 1 to 5.

The present invention further relates to a method for inhibiting the growth of weeds, particularly velvetleaf plants, comprising contacting at least part of the weed with a herbicidal formulation, the improvement comprising using as said herbicidal formulation a homogeneous aqueous dispersion of the aforementioned composition.

DETAILED DESCRIPTION OF THE INVENTION

The herbicidal composition of the present invention is a homogeneous mixture consisting essentially of (I) a postemergent herbicide, (II) a silicone glycol adjuvant consisting essentially of (i) an acetoxy-terminated silicone glycol having seven ethylene oxide units in its glycol chain and (ii) a silicone glycol dispersant for silicone glycol (i).

The postemergent herbicide (I) of the present invention is selected from those herbicides well known in the art to be effective when applied after the emergence of a plant. Examples of such postemergent herbicides include, inter alia, 3-isopropyl-1H-2,1,3-benzothiadiazin-4(3H)-one 2,2-dioxide (bentazon) and N-(phosphonomethyl)glycine (glyphosate). The former herbicide is marketed under the trade name BASAGRAN by BASF Wyandotte Corp., Parsippany, N.J. and the latter herbicide is sold under the trade name ROUNDUP by Monsanto Agricultural Products Co., St. Louis, Mo.

For the purposes of the present invention, the herbicide is preferably selected from the diphenyl ether structures exemplified by the general formula

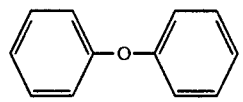

Specific examples of this class of herbicides include such compounds as 2,4-dichlorophenyl 4-nitrophenyl ether (nitrofen); 5-(2-chloro-4-trifluoromethylphenoxy)-2-nitrobenzoic acid (acifluorofen); ethoxycarbonylmethyl 2-[3-(2,6-dichloro-4-trifluoromethyl-phenoxy)-6-nitrophenoxy]-propionate; ethoxymethyl 2-[3-(chloro-4-trifluoromethyl-phenoxy)-6-nitrophenoxy]-propionate; sodium 5-[2-chloro-4-(trifuoromethyl)-phenoxy]-2-nitrobenzoate (acifluorfen-sodium); methyl 5-(2,4-dichlorophenoxy)-2-nitrobenzoate (bifenox); and 2-chloro-1-(3-ethoxy-4-nitrophenoxy)-4-(trifluoromethyl) benzene (oxyfluorfen). For the purposes of the present invention, acifluorfen-sodium is a preferred herbicide.

The silicone glycol (i) of the present invention has the average structure

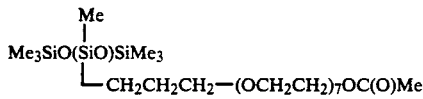

wherein Me hereinafter denotes a methyl radical. The silicone glycol (i) may be prepared by coupling the corresponding allyl-terminated glycol to a bis-siloxane structure having a hydrogen attached to the central silicon atom, said structure being

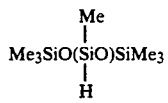

Generally, the coupling is accomplished in the presence of a platinum catalyst. The skilled artisan will recognize that, in such coupling reactions, a fraction of the allyl-terminated glycol is not converted and will remain as an impurity in the final silicone glycol product. Additionally, as a result of inefficient distillation, the allyl-terminated glycol employed may contain a minor proportion of molecules having less than 7, or more than 7, ethylene oxide units. This, in turn, results in silicone glycols having less than 7 or greater than 7 ethylene oxide units, respectively. The herbicide compositions may contain such impurities and still be within the scope of the present invention.

The silicone glycol dispersant (ii) of the present invention is similar to the above described silicone glycol (i) and has the average formula

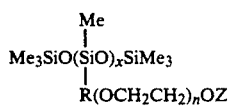

wherein R is a divalent alkylene group having 2 to 6 carbon atoms, Z is selected from the group consisting of hydrogen, an alkyl radical having 1 to 3 carbon atoms and an acyl group having 2 to 4 carbon atoms, n is 8 to 24 and x is 1 to 5. It is preferred that x is 1 and n is about 12.

A highly preferred silicone glycol dispersant of the present invention has the average structure

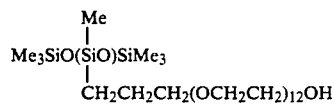

In addition to the aforementioned components, the compositions of the present invention may also contain other herbicide adjuvants commonly employed in the art. Examples of such adjuvants include crop oil concentrate, ORTHO X-77 spreader, drift control agents, such as LO-DRIFT, defoaming agents, such as D-FOAMER, other compatibility agents, such as E-Z MIX, and other adjuvants well known in the herbicide art.

In order to prepare the compositions of the present invention, from about 20 to 95 weight percent of silicone glycol (i) is first thoroughly mixed with from about 80 to 5 weight percent of the silicone glycol dispersant (ii) to form the silicone glycol adjuvant (II). The optimum ratio of these ingredients dependent upon the particular silicone glycol dispersant employed and is readily determined through routine experimentation by the skilled artisan.

The above mentioned silicone glycol adjuvant (II) is then preferably blended with herbicide (I) to form a homogeneous dispersion which can then be diluted with water and sprayed onto plants according to the method of the present invention, described infra. Alternatively, the silicone glycol adjuvant (II) may be added directly to a water solution or dispersion of herbicide (I).

In order to be within the scope of the present invention, from about 0.01 to 50 parts by weight of the silicone glycol adjuvant (II) are used for each part by weight of herbicide (I). Preferably, from about 0.2 to 17 parts by weight of the silicone glycol adjuvant (II) are so employed.

Preferred embodiments of the present invention employ silicone glycol (i) and the highly preferred silicone glycol dispersant, described above, in a weight ratio of about 2:1 to 9:1, respectively. In a particularly preferred embodiment, this ratio is 4:1 and about 5 parts by weight of silicone glycol adjuvant (II) is used for each part by weight of herbicide (I).

In another aspect, the compositions of the present invention consist essentially of from about 0.02 to 2.0 parts by weight of postemergent herbicide (I), from about 0.01 to 50 parts by weight, for each part by weight of said herbicide (I), of the silicone glycol adjuvant (II) and sufficient water to provide 100 parts by weight of the total composition.

The present invention also relates to a method for inhibiting the growth of weeds, particularly the species Abutilon theophrasti, hereinafter referred to by its common name of "velvetleaf." This method comprises contacting at least part of the weed with a homogeneous water dispersion of a herbicidal composition, as hereinabove described. This water dispersion is applied to the foliage of the weed by any of the methods commonly practiced in the art, preferably by spraying. The amount of the dispersion, and the herbicide contained therein, to be applied to the velvetleaf may be varied to a great extent, the optima being determined by such factors as soil conditions, weather conditions and the type of crops or other plants growing alongside the weed. Generally, however, the effective range is about 0.12 to 2 pounds per acre of herbicide formulation.

When the compositions of the present invention are used according to the above described method, there is observed a marked improvement in the rainfastness of the herbicide compositions relative to those containing silicone glycol adjuvants having (on average) seven ethylene oxide units in the glycol chain wherein said glycol chain is not terminated with an acetoxy group. Thus, when compared with currently used silicone glycol adjuvants, there is provided a distinct advantage by the instant compositions in that they permit the use of lower herbicide levels to attain a similar degree of injury to a weed when there is a reasonable likelihood of precipitation after broadcasting the herbicide. Such a reduction in herbicide levels generally results in reduced insult to adjacent cash crops and is considered highly desirable.

EXAMPLES

The following examples are presented to further illustrate the compositions of this invention, but are not to be construed as limiting the invention, which is delineated in the appended claims. All parts and percentages in the examples are on a weight basis unless indicated to the contrary.

Silicone glycols, having the average structure

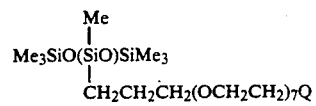

wherein Me hereinafter denotes a methyl radical and Q is defined in Table 1, were prepared by the platinum catalyzed addition of the appropriate allyl-terminated glycol to an organohydrogenpolysiloxane having the structure

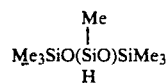

In Table 1, SILICONE GLYCOLE C is a commercial silicone glycol, SILWET L-77 (Union Carbide Corp., Danbury, Conn.), and is believed to have the above structure wherein the glycol chain is terminated by a methoxy group.

TABLE 1

| Silicone Glycol | Terminal Group Q | |
|---|---|---|
| SILICONE GLYCOL A | —OC(O)Me | (Acetoxy) |
| SILICONE GLYCOL B | —OH | (Hydroxyl) |
| SILICONE GLYCOL C* | —OMe | (Methoxy) |
| SILICONE GLYCOL D | —OC(O)CH$_2$Me | (Propionate) |
| SILICONE GLYCOL E | —OC(O)CH$_2$CH$_2$COOH | (Succinate) |

*SILWET L-77 (Union Carbide Corp., Danbury, CT)

A silicone glycol having the average structure

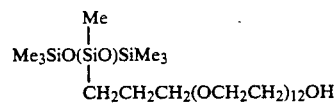

was employed as the dispersant for the above described silicone glycols, and will be referred to as DISPERSANT 1 herein.

The herbicide used in the examples was acifluorfen-sodium marketed by BASF Corporation (Research Triangle Park, N.C.) under the trade name BLAZER.

EXAMPLES 1–10

Water dispersions of herbicidal compositions were prepared by first thoroughly mixing the amount of SILICONE GLYCOL A through SILICONE GLYCOL C indicated in Table 2 with the amount of DISPERSANT 1. These mixtures were then blended with BLAZER (0.18 gm each) and each blend was diluted with water to provide 250 ml of total dispersion.

TEST PROTOCOL

Individually potted velvetleaf plants were grown under standard greenhouse conditions in BACCTO professional potting soil mix. Temperature was controlled at 75+/−2° F. Irradiation consisted of normal sunlight supplemented by high-pressure sodium vapor lamps to provide an added 1,200 $\mu$E/m$^2$·s at bench level ($\mu$E =microeinstein), wherein the day/night cycle was set at 18 hours and 6 hours, respectively.

When the plants were 3 to 5 inches tall, they were sprayed with water dispersions of the herbicide compositions so as to broadcast herbicide (i.e., BLAZER) at a rate of 0.03 pounds per acre (0.03 lb/A) along with the adjuvant (i.e., silicone glycol plus dispersant, when used). The adjuvant rate was ⅜ pint/A when 0.94 grams of total adjuvant was used. Spraying was accomplished by means of a link-belt sprayer fitted with a TEEJET 8001 E nozzle which delivered the equivalent of 25 gallons/acre of the herbicide dispersion. In the spray apparatus employed, the 250 ml samples, described above, provided the prescribed broadcast rates.

In addition, the rainfastness of the herbicide compositions was evaluated by spraying half the plants with water in order to simulate rainfall. This procedure consisted of spraying plants from above (8-10 inches above plant tops) using a TEEJET nozzle which delivered 0.4 gallons of water per minute. This nozzle was also mounted on a chain drive and reciprocally moved over four plants at a time, each such traverse taking about 9-10 seconds. The water spray was started 15 minutes after application of the herbicide compositions and was continued for approximately 7 minutes, at which point the equivalent of one inch of "rain" had fallen on each plant.

Plant injury was visually determined using a double-blind experimental mode wherein four replicates were run for each herbicide composition. Phytotoxicity was ranked from zero, corresponding to no observable effect, to 100%, corresponding to total destruction of the plant. These results were averaged and the values reported using Duncan's multiple range test to distinguish statistical differences at the 95% confidence level. As is common practice in the art, the injury values reported infra include lower case superscript letters which indicate whether any given set of values is statistically identical. Thus, for example, when two injury values have such a superscript in common, this is an indication that these values are not statistically different at the 5% level by Duncan's method.

The above described herbicide dispersions were used to spray velvetleaf plants and the degree of injury, both with and without rain simulation, was observed seven days after spraying with the herbicide dispersions of Examples 1-3. These results, along with the Duncan statistical annotations, are presented in Table 2. As a control, four velvetleaf plants were observed which were not sprayed with any herbicide composition.

TABLE 2

| Example | SILICONE GLYCOL Type | SILICONE GLYCOL Amount (gm) | DISPERSANT 1 Amount (gm) | Percent Injury to Plant No Rain | Percent Injury to Plant With Rain |
|---|---|---|---|---|---|
| 1 | A | 0.752 | 0.188 | 74$^{d,e}$ | 71$^{e,f}$ |
| 2 | A | 1.25 | — | 60$^g$ | 41$^{j,k}$ |
| 3 | — | — | 0.94 | 40$^{j,k}$ | 5$^{r,s}$ |
| 4 | — | — | 0.752 | 38$^{j,k,l}$ | 5$^{r,s}$ |
| 5 | — | — | 0.188 | 15$^{p,q}$ | 0$^s$ |
| 6 | B | 0.752 | 0.188 | 83$^{a,b,c}$ | 33$^{l,m}$ |
| 7 | C | 0.752 | 0.188 | 88$^a$ | 43$^{i,j,k}$ |
| 8 | C | 0.94 | — | 80$^{b,c,d}$ | 44$^{h,i,j}$ |
| 9 | C | 0.752 | — | 81$^{a,b,c}$ | 36$^{k,l,m}$ |
| 10 | — | — | (BLAZER alone) | 0$^s$ | 0$^s$ |
| Control-(No BLAZER, No adjuvants) | | | | 0$^s$ | 0$^s$ |

It is apparent from Table 2 that the herbicide formulation containing the silicone glycol having acetoxy-terminated glycol chains, in combination with DISPERSANT 1, provided significantly improved phytotoxicity after exposure to simulated rain conditions relative to the corresponding hydroxyl- and methoxy-terminated compounds. Furthermore, it is seen that DISPERSANT 1, SILICONE GLYCOL B and SILICONE GLYCOL C did not provide the improved rainfastness as did the combination of DISPERSANT 1 and SILICONE GLYCOL A when a total of 0.94 grams of each adjuvant was employed in the herbicidal composition. SILICONE GLYCOL A was less effective than the combination even when employed at a higher concentration (i.e., 1.25 gm).

EXAMPLES 11-16

Herbicidal composition were prepared and tested according to the procedures of Examples 1-10 wherein only 0.94 grams of the silicone glycols shown in Table 3 were mixed with 0.14 ml (0.18 gm) of BLAZER (i.e., no DISPERSANT 1 was added). As before, the herbicidal compositions were applied to velvetleaf at a rate of 0.03 lb/A of BLAZER and ¾ pint/A of the silicone glycol adjuvant. Table 3 indicates that essentially no improvement in rainfastness is obtained by varying the glycol chain terminal groups when the dispersant was omitted.

TABLE 3

| Example | SILICONE GLYCOL Type | SILICONE GLYCOL End Group | Percent Injury to Plant No Rain | Percent Injury to Plant With Rain |
|---|---|---|---|---|
| 11 | A | Acetoxy | 74$^a$ | 30$^{f,g}$ |
| 12 | B | Hydroxyl | 73$^a$ | 28$^{f,g,h}$ |
| 13 | C | Methoxy | 63$^{b,c}$ | 33$^{e,f,g}$ |
| 14 | D | Propionate | 70$^{a,b}$ | 35$^{e,f}$ |
| 15 | E | Succinate | 18$^{h,i,j}$ | 0$^k$ |
| 16 | (BLAZER alone) | | 0$^k$ | 0$^k$ |
| Control-(No BLAZER, No adjuvants) | | | 0$^k$ | 0$^k$ |

We claim:

1. A silicone glycol having the structure

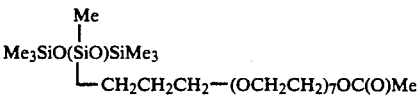

wherein Me denotes a methyl radical.

* * * * *